United States Patent [19]
Trautmann et al.

[11] Patent Number: 5,307,819
[45] Date of Patent: May 3, 1994

[54] METHOD AND APPARATUS FOR CONTAINING ANATOMICAL MATERIAL PRODUCED BY A PATIENT

[75] Inventors: Marlane M. Trautmann, 224 McKinley Ave., Pittsburgh, Pa. 15202; Ansel M. Schwartz, 5514 Claybourne St., Pittsburgh, Pa. 15232

[73] Assignees: Marlane M. Trautmann; Ansel M. Schwartz, Pittsburgh, Pa.

[21] Appl. No.: 929,732

[22] Filed: Aug. 13, 1992

[51] Int. Cl.⁵ .............................................. A61B 5/00
[52] U.S. Cl. ..................................... 128/767; 128/771; 604/317; 604/410; 604/416
[58] Field of Search ............... 128/760, 762, 767, 771, 128/770; 206/204; 604/87, 88, 89, 318, 319, 321, 322, 323, 326, 336, 346, 347, 349, 350, 408, 410, 416, 56, 317

[56] References Cited

U.S. PATENT DOCUMENTS

| | | | |
|---|---|---|---|
| 3,952,729 | 4/1976 | Libman et al. | 128/762 |
| 4,305,406 | 12/1981 | Meisch | 128/762 |
| 4,602,910 | 7/1986 | Larkin | 604/87 |
| 4,608,043 | 8/1986 | Larkin | 604/87 |
| 4,700,714 | 10/1987 | Fuisz | 128/767 |
| 4,820,291 | 4/1989 | Terauchi et al. | 604/349 |
| 4,994,056 | 2/1991 | Ikeda | 604/410 |
| 4,994,057 | 2/1991 | Carmen et al. | 604/416 |
| 5,092,858 | 3/1992 | Benson et al. | 604/319 |
| 5,102,408 | 4/1992 | Hamacher | 604/416 |

FOREIGN PATENT DOCUMENTS

| | | | |
|---|---|---|---|
| 3837856 | 5/1989 | Fed. Rep. of Germany | 128/760 |
| 2507080 | 12/1982 | France | 128/760 |
| 1-314964 | 12/1989 | Japan | 128/760 |
| 2239804 | 7/1991 | United Kingdom | 604/349 |

Primary Examiner—Stephen C. Pellegrino
Assistant Examiner—Guy V. Tucker
Attorney, Agent, or Firm—Ansel M. Schwartz

[57] ABSTRACT

The present invention pertains to an apparatus for containing material produced by a patient. The apparatus is comprised of a container having a first portion with a first cavity within which the anatomical material is held and an opening through which the anatomical material is provided to the first cavity. The apparatus is also comprised of a second portion with a second cavity in communication with the first cavity, and a removable seal disposed between the first cavity and the second cavity. Additionally, the apparatus is comprised of an immobilizing material disposed in the first portion, which when the seal is removed between the first cavity and second cavity mixes with patient material and immobilizes it. The present invention also pertains to a method for collecting anatomical material produced by a patient. The method comprises the steps of placing or collecting the anatomical material into a first cavity of a first portion of a container. Then, there is the step of releasing immobilizing material from a second cavity of a second portion of the container in communication with the first cavity into the first cavity so the anatomical material is immobilized in the first cavity.

11 Claims, 4 Drawing Sheets

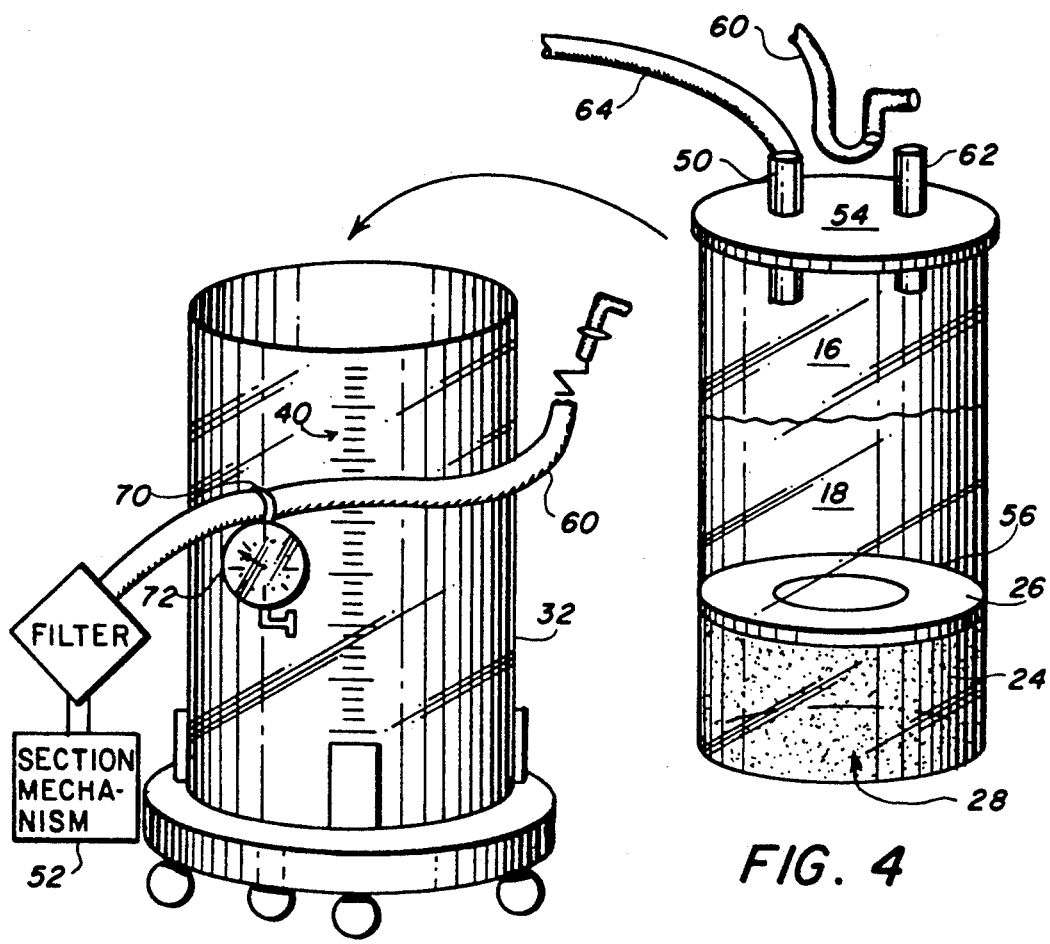
FIG. 4
FIG. 5
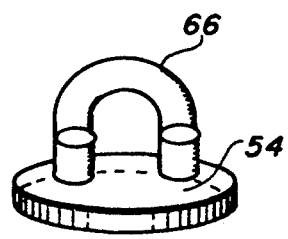
FIG. 6

METHOD AND APPARATUS FOR CONTAINING ANATOMICAL MATERIAL PRODUCED BY A PATIENT

FIELD OF THE INVENTION

The present invention pertains to a method and apparatus for containing anatomical material produced by a patient. More specifically, the present invention pertains to a method and apparatus for containing urine by immobilizing it for transportation.

BACKGROUND OF THE INVENTION

At the advent of auto-immune deficiency syndrome (AIDS), great attention has come upon the medical technician-patient relationship. In order to protect both the medical technician from the patient and vice versa, efforts are being taken throughout the medical industry to isolate these relationships so that no real physical contact occurs therebetween. One example of this problem is with respect to anatomical material produced by a patient such as urine which occurs in large quantities with patients on a frequent and consistent basis and requires efficient and safe handling techniques for disposal. The present invention is a method and apparatus for containing anatomical material produced by a patient so that removal of the same can occur safely and efficiently.

SUMMARY OF THE INVENTION

The present invention pertains to an apparatus for containing material produced by a patient. The apparatus is comprised of a container having a first portion with a first cavity within which the anatomical material is held and an opening through which the anatomical material is provided to the first cavity. The apparatus is also comprised of a second portion with a second cavity in communication with the first cavity, and a removable seal disposed between the first cavity and the second cavity. Additionally, the apparatus is comprised of an immobilizing material disposed in the first portion, which when the seal no longer exists removed between the first cavity and second cavity, mixes with patient material and immobilizes it.

The present invention also pertains to a method for collecting anatomical material produced by a patient. The method comprises the steps of introducing the anatomical material into a first cavity of a first portion of a container. Then, there is the step of releasing immobilizing material from a second cavity of a second portion of the container in communication with the first cavity into the first cavity so the anatomical material is immobilized in the first cavity.

BRIEF DESCRIPTION OF THE DRAWINGS

In the accompanying drawings, the preferred embodiment of the invention and preferred methods of practicing the invention are illustrated in which:

FIG. 4 is a schematic representation of an alternative embodiment of a container of the present invention.

FIG. 5 is a schematic representation of an alternative embodiment of a holder of the present invention.

FIG. 6 is a schematic representation of a rigid top having closure tubing.

DESCRIPTION OF THE PREFERRED EMBODIMENT

Figure 1:
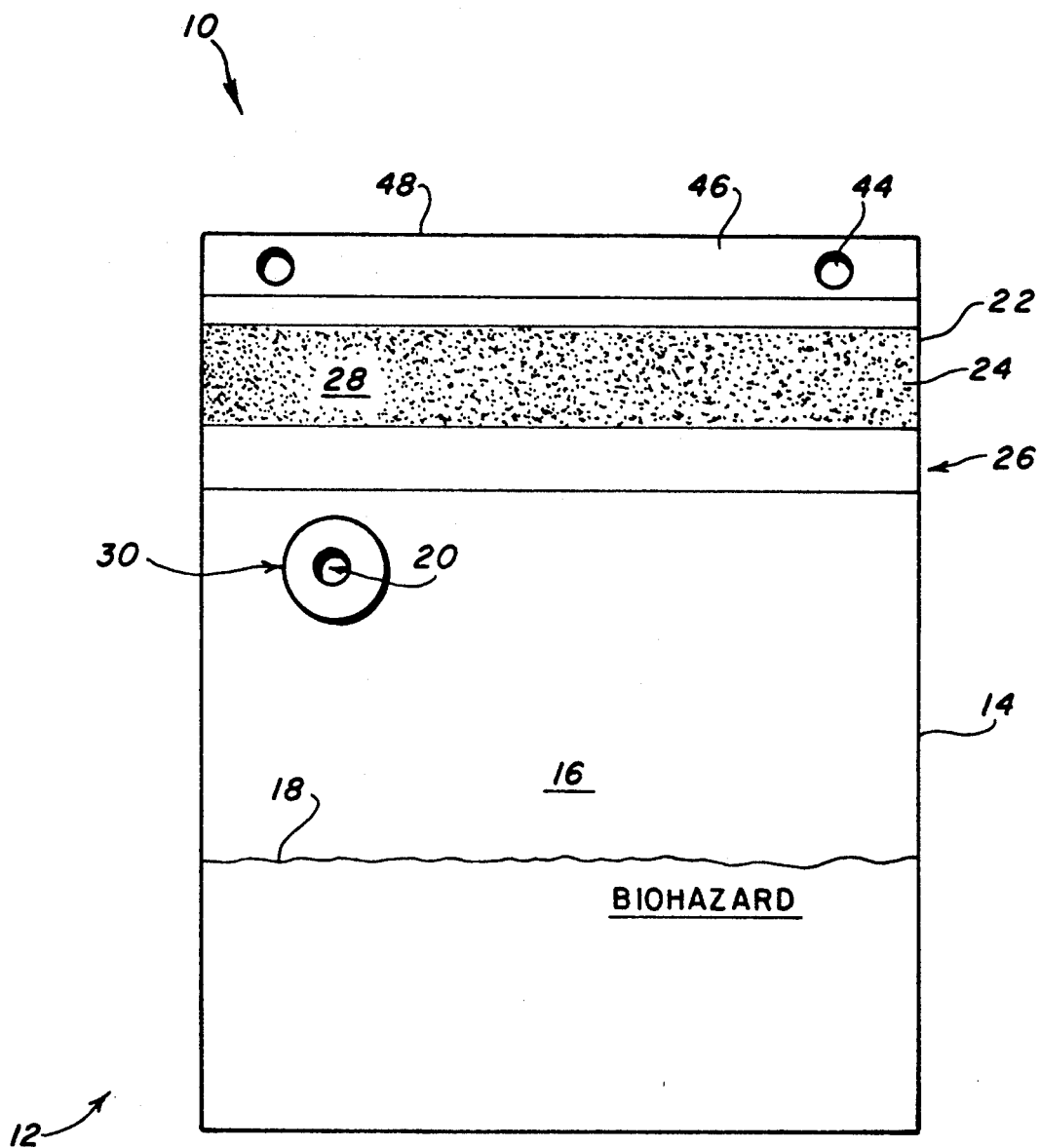
FIG. 1 is a schematic representation of a container for an apparatus for containing anatomical material produced by a patient.

Referring now to the drawings wherein like reference numerals refer to similar or identical parts throughout the several views, and more specifically to FIG. 1 thereof, there is shown a perspective view of an apparatus 10 for containing anatomical material produced by a patient. The anatomical material can be, for instance, anything excreted, grown or issued by a body of a patient such as blood, tissue, fecal matter, bile, plasma, dialysis waste or preferably urine to name but a few of the many possible examples. More, it can also include fluid such as irrigation fluid which is introduced into the patient and thus comes into contact with the patient and is contaminated thereby. The apparatus 10 is comprised of a container 12 having a first portion 14 with a first cavity 16 within which the anatomical material 18 is held and an opening 20 through which the anatomical material 18 is provided to the first cavity 16. The apparatus 10 is also comprised of a second portion 22 with a second cavity 24 in communication with the first cavity 16 and a removable seal 26 disposed between the first cavity 16 and the second cavity 24. Additionally, there is an immobilizing material 28 disposed in the first portion 14, which when the seal 26 no longer exists between the first cavity 16 and second cavity 24, mixes with patient anatomical material 18 and immobilizes it. The immobilizing material 28 can be, for instance, a solidifying or gelling material which causes the anatomical material to gel so it becomes more containable and is more easily prevented from spreading or leaking, such as Isolyser ™ LTS22000. The immobilizing material 28 can include a neutralizing agent such as a bacteriocidal and, or an anti-viral agent, or both. Lye or bleach which kills any virus or bacteria present in the anatomical material, or all these types of material 28 together.

Figure 2:
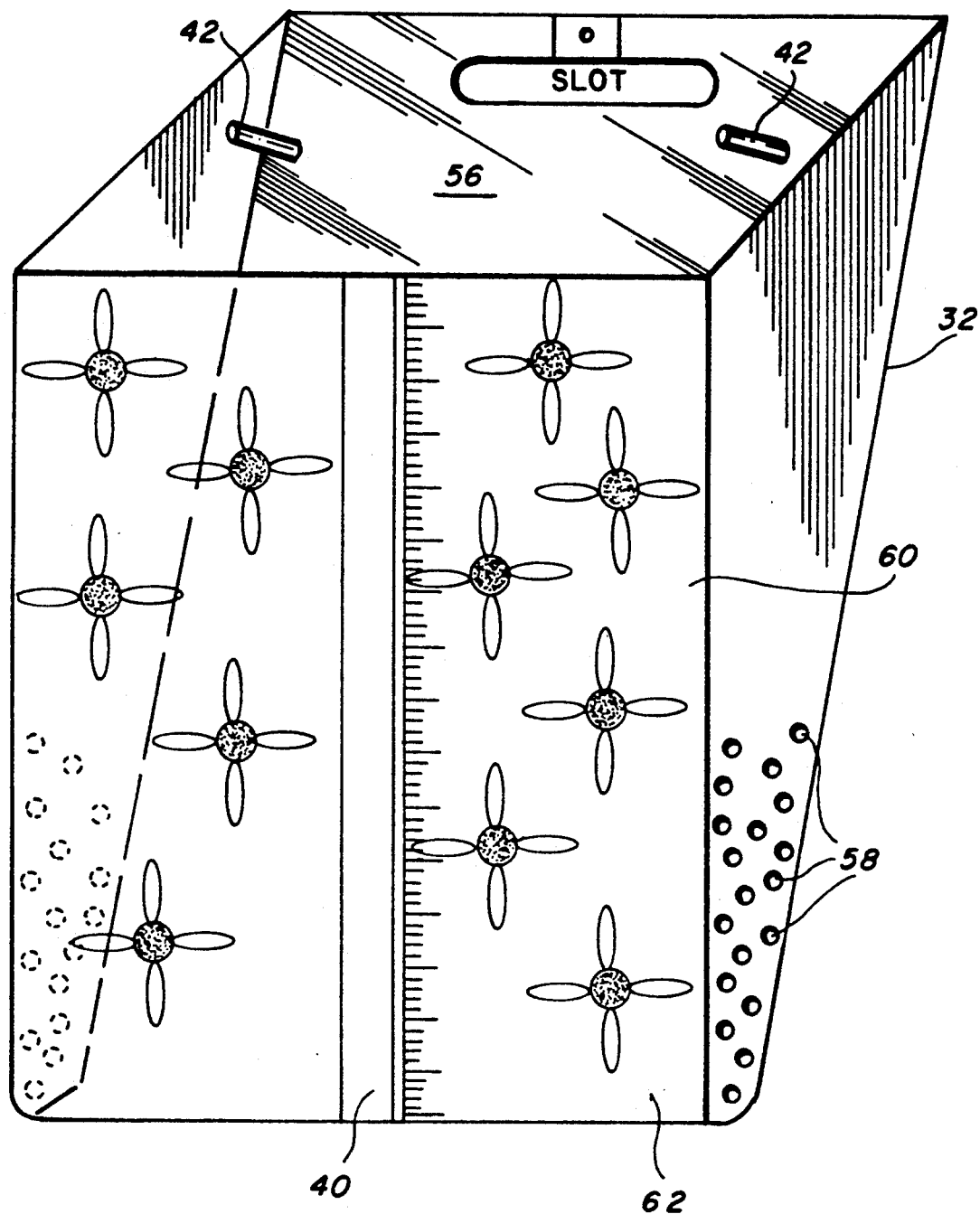
FIG. 2 is a schematic representation of a holder for a container of anatomical material produced by a patient.

Preferably, the container 12 includes a one-way valve 30 disposed in the first portion 14 which defines the opening 20. As shown in FIG. 2, there can also be a holder 32 for the container 12 within which the container 12 is disposed. For ease of illustration, the holder 32 is shown without the container 12 in FIG. 2. The apparatus 10 also preferably includes a tube 34 which is removably attached to the first portion 14 and which has a first end 36 in contact with the first cavity 16. The tube 34 provides a channel 38 through which patient anatomical material 18 is provided to the first cavity 16.

The holder 32 preferably has calibration 40 to identify how much anatomical patient material 18 is in the first cavity 16. The holder also preferably has a mechanism for securing the container 12 to the holder 32. The securing mechanism can be, for instance, velcro, thumbtacks, nails or preferably pegs 42 through which holes 44 disposed on a strip 46 at the top 48 of the container 12 and extending from the first portion 14.

The present invention also pertains to a method for collecting anatomical material 18 produced by a patient. The method comprises the steps of introducing the anatomical patient material 18 into the first cavity 16 of the first portion 14 of the container 12. Then there is the step of releasing immobilizing material 28 from a second cavity 24 of a second portion 22 of the container 12 in communication with the first cavity 16 into the first cavity 16 so the anatomical patient material 18 is immobilized in the first cavity 16. Preferably, the introducing step includes the step of connecting the tube 34 to the first cavity 16 of the first portion 14 to introduce anatomical patient material 18 into the first cavity 16.

In the operation of the preferred embodiment, three times a day, at approximately each nursing change of shift, a plastic container 12 having urine therein is removed and a new container 12 is placed in the holder 32 that is attached on the side of a bed or wheelchair of a patient. The container 12 is placed on the holder 32 by way of holes 44 on a strip 46 at the top 48 of the container 12 being placed on pegs 42 that extend out of the top of the holder 32. When the holder 32 has the container 12 on the pegs 42, then a plastic tube 34 has its first end 36 inserted into an opening 20 in one-way valve 30. The other end 50 of the tube 34 is connected to a catheter (not shown) that is present in a patient.

Figure 3A:
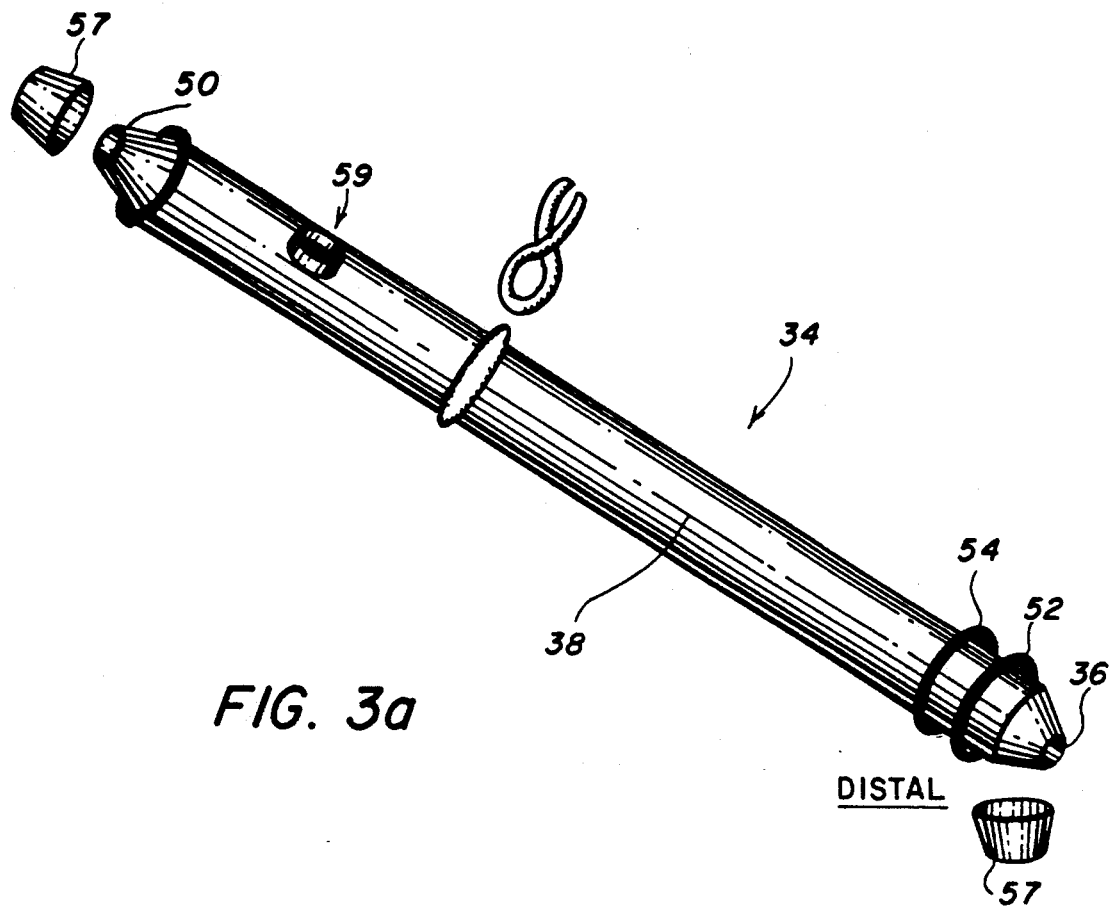
FIGS. 3a and 3b are schematic representations of a tube which communicates with the container of the present invention and the patient.
Figure 3B:
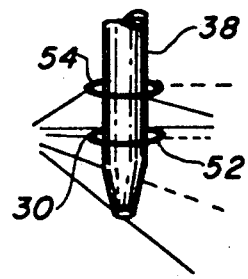

The tube 34, as shown in FIG. 3a, has on its first end 36 a first collar 52 and a second collar 54, each of which are soft retention rings. The first collar 52 is pushed through the one-way valve 30, as shown in FIG. 3b. In this way, the tube 34 is securely maintained in communication with the first cavity 16 of the container 12 such that urine flows directly therein as shown in FIG. 3. The tube 34 can be, for instance, a modified Bard TM tube. The tube 34 has covers 57 for each end, a clip to attach to an object such as a bed liner, and an aspiration hole 59.

At desired times, a nurse or medical technician can record for the patient's records the amount of urine in the container 12 by reviewing the calibration 40 on the holder 32. The holder 32 on its backside 56 can have a covering of white to more easily enable the nurse or medical technician to read the calibration and the corresponding level of urine in the first portion 14 of the container 12. The holder 32 can also have air holes 58 to enable the container 12 to settle properly in the holder 32. The front side 60 of the holder 32 can have decorations 62.

When the time comes to change the container 12, a technician removes the tube 34 from the one-way valve 30 by pulling it out. The one-way valve 30 prevents any urine from escaping the bag. The container 12 is then lifted off of the pegs 42 of the holder 32. The nurse or technician then grasps opposite sides of the container 12 and pulls them apart. This action causes the seal 36, which is, for instance, a zip lock strip to open allowing Isolyser TM LTS 22000 or other suitable chemicals on the market to be released from the second portion 22 and fall into the first cavity 16. In doing so, the Isolyser TM LTS 22000 mixes with the urine causing it to gel for easy handling and disposal. As per O.S.H.A. requirements, a standard biohazard label can be imprinted on the apparatus 10.

The formation of the container 12 involves well known plastic bag production techniques.

In an alternative embodiment as shown in FIGS. 4 and 5, a container 12 can have an input port 50 in fluidic communication with the first cavity 16. There can also be a suction mechanism 52 such as a vacuum pump, in fluidic communication with the first cavity 16 to draw anatomical patient material into the first cavity 16 preferably through the input port 50. The container 12 can include a rigid top 54 to which it is removably and sealingly attached to rigid top 54. There can be a pressure valve 57 disposed in a seal 26 in the container 12 which separates the first cavity 16 with the second cavity 24. In the second cavity 24 is the immobilizing material 28.

There is a vacuum tube 60 connected to a second port 62 of the container 12, preferably disposed in the rigid top 54 to cause the suction to the first cavity 16 which in turn causes anatomical material to be drawn from the patient through the input port 50 by way of patient tubing 64. The presence of the suction in the first cavity 16 by way of the second tube 62 maintains the vacuum valve 36 in a closed position. Alternatively, the vacuum valve 36 can be a one-way valve which only opens when the container 12 is turned upside down such that the second portion 24 is above the first portion 16 thus releasing the immobilizing material 28 into the first cavity 16 having the anatomical material therein.

When the container 12 is to have the immobilizing material 28 mixed with the anatomical material in the first cavity 16, the patient tubing 64 and the vacuum tubing 60 are removed from the input port 15 and the second port 62, respectively, and a closure tube 66 is connected to the input port 50 and the second port 62 as shown in FIG. 6 so no material escapes from the container 12.

The holder 32, as shown in FIG. 5, is open at its top into which the container 12 is introduced and the rigid top 54 rests against and preferably snaps into. There is calibration 40 on the side of the holder 32 to measure the amount of anatomical material in the container 12. There can be a holder 70 to maintain the vacuum tubing 60 in proximity to the holder 32 so it does not get tangled or caught on an object, and there can be a vacuum gauge 72 disposed on the holder 32 to indicate the amount of suction in the vacuum tubing 60.

Although the invention has been described in detail in the foregoing embodiments for the purpose of illustration, it is to be understood that such detail is solely for that purpose and that variations can be made therein by those skilled in the art without departing from the spirit and scope of the invention except as it may be described by the following claims.

What is claimed is:

1. An apparatus for containing anatomical material produced by a patient comprising:

a container having opposing sides and a first portion with a first cavity within which the anatomical material is to be held and an opening through which the anatomical material is provided to the first cavity, said container having a second portion with a second cavity disposed adjacent to the first cavity;

a removable mechanically separable seal separating the first cavity and the second cavity, said seal removable by pulling on the opposing sides of the container; and an immobilizing material disposed in the second portion, which when the seal is pulled apart and no longer exists between the first cavity and second cavity mixes with the anatomical material and causes it to solidify or gel.

2. An apparatus as described in claim 1 including a one way valve disposed in the first portion which defines the opening.

3. An apparatus as described in claim 2 including a holder for the container within which the container is disposed.

4. An apparatus as described in claim 3 including a tube which is removably attached to the first portion and which has a first end in contact with the first cavity, said tube providing a channel through which patient anatomical material is provided to the first cavity.

5. An apparatus as described in claim 4 wherein the holder has calibration to identify how much anatomical patient material is in the first cavity.

6. An apparatus as described in claim 1 wherein the immobilizing material comprises a neutralizing agent which kills any virus or bacteria in the anatomical material.

7. An apparatus as described in claim 6 wherein the neutralizing agent is bleach.

8. A method for collecting anatomical material produced by a patient comprising the steps of:
   introducing the anatomical material into a first cavity of a first portion of a container; and
   releasing immobilizing material from a second cavity of a second portion of the container adjacent to and removably sealed from the first cavity into the first cavity by pulling on opposing sides of the container and thereby pulling apart the seal so the anatomical material is solidified or gelled in the first cavity.

9. A method as described in claim 7 wherein the introducing step includes the step of connecting a tube to the first cavity of the first portion to introduce anatomical patient material into the first cavity.

10. An apparatus for containing anatomical material produced by a patient comprising:
    a container having opposing sides and a first portion with a first cavity within which the anatomical material is to be held and an opening through which the anatomical material is provided to the first cavity, said container having a second portion with a second cavity disposed adjacent to the first cavity;
    a removable seal separating the first cavity and the second cavity, said seal removable by pulling on the opposing sides of the container; and
    an immobilizing material disposed in the second portion, which when the seal is pulled apart and no longer exists between the first cavity and second cavity mixes with the anatomical material and kills any virus or bacteria in the anatomical material.

11. A method for collecting anatomical material produced by a patient comprising the steps of:
    introducing the anatomical material into a first cavity of a first portion of a container; and
    releasing immobilizing material from a second cavity of a second portion of the container adjacent to an removably sealed from the first cavity into the first cavity by pulling on opposing sides of the container and thereby pulling apart the seal so an virus or bacteria in the anatomical material is killed.

\* \* \* \* \*